United States Patent [19]

Pigerol et al.

[11] 4,139,634
[45] Feb. 13, 1979

[54] INDOLE DERIVATIVES AND PROCESS FOR PREPARING THE SAME

[75] Inventors: Charles Pigerol, Saint-Ouen; Paul de Cointet de Fillain, Sisteron; Pierre Eymard, Fontaine; Jean-Pierre Werbenec, Eysines; Madeleine Broll, St. Egreve, all of France

[73] Assignee: Labaz, Paris, France

[21] Appl. No.: 798,802

[22] Filed: May 20, 1977

[30] Foreign Application Priority Data

Jun. 17, 1976 [FR] France .......................... 76 18364

[51] Int. Cl.$^2$ ................ A61K 31/40; C07D 209/08; C07D 209/30; C07D 401/06
[52] U.S. Cl. .................................. 424/274; 546/248; 546/201; 546/184; 546/245; 260/326.12 R; 260/326.14 R; 260/326.15; 424/250; 424/267; 544/143; 544/144; 544/373
[58] Field of Search ............... 260/326.12 R, 326.15, 260/326.14; 424/274

[56] References Cited

U.S. PATENT DOCUMENTS 3,503,990 3/1970 Shoen et al. ............ 260/326.12 R

FOREIGN PATENT DOCUMENTS 224635 5/1962 Austria ........................... 260/326.15

OTHER PUBLICATIONS

Kaji et al., Chem. Abstracts, vol. 47, cols. 9317-9318 (1953).

Primary Examiner—Alton D. Rollins
Attorney, Agent, or Firm—Mason, Kolehmainen, Rathburn & Wyss

[57] ABSTRACT

Indole derivatives of the formula:

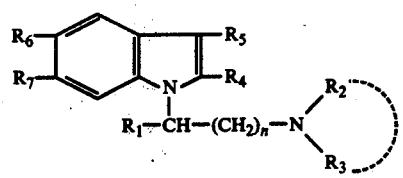

I wherein $R_1$ represents a hydrogen atom or a methyl radical, $R_2$ and $R_3$, which are the same or different, each represent a hydrogen atom, a methyl or ethyl radical, a benzyl radical or represent together a pentamethylene, hexamethylene, oxydiethylene or N-methylaminodiethylene chain, forming thus a cycle with the nitrogen atom, $R_4$ represents a phenyl, 2', 4'-dimethyl-phenyl, isopropyl, cyclopropyl, 1-methyl-cyclopropyl, cyclopentyl or cyclohexyl radical, $R_5$ represents a hydrogen atom, a branched- or straight-chain alkyl radical containing from 1 to 3 carbon atoms, a methylthio or ethylthio radical or a straight-chain acyl radical containing from 2 to 6 carbon atoms, $R_6$ represents a hydrogen atom or a halogen atom, a methyl, methoxy, hydroxy, carboxy, nitro, amino, methylamino or dimethylamino radical, $R_7$ represents a hydrogen atom or a halogen atom and n is 1 or 2, with the proviso that two at least of the groups $R_5$, $R_6$ and $R_7$ represent a hydrogen atom and that, when n is 2, one at least of the groups $R_2$ and $R_3$ is not a hydrogen atom, and their pharmaceutically acceptable acid addition salts.

The derivatives of the invention are useful as antidepressant and/or antiaggressive agents.

8 Claims, No Drawings

NEW INDOLE DERIVATIVES AND PROCESS FOR PREPARING THE SAME

This invention relates to novel indole derivatives, to a process for preparing said novel indole derivatives and to pharmaceutical compositions containing them.

The indole derivatives with which the invention is concerned are represented by the general formula:

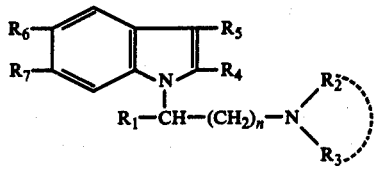

wherein $R_1$ represents a hydrogen atom or a methyl radical, $R_2$ and $R_3$, which are the same or different, each represent a hydrogen atom, a methyl or ethyl radical, a benzyl radical or represent together a pentamethylene, hexamethylene, oxydiethylene or N-methylaminodiethylene chain, forming thus a cycle with the nitrogen atom, $R_4$ represents a phenyl, 2',4'-dimethyl phenyl, isopropyl, cyclopropyl, 1-methyl cyclopropyl, cyclopentyl or cyclohexyl radical $R_5$ represents a hydrogen atom, a branched- or straight-chain alkyl radical containing from 1 to 3 carbon atoms, a methylthio or ethylthio radical or a straight-chain acyl radical containing from 2 to 6 carbon atoms, $R_6$ represents a hydrogen atom or a halogen atom, preferably a chlorine or bromine atom, a methyl, methoxy, hydroxy, carboxy, nitro, amino, methylamino or dimethylamino radical, $R_7$ represents a hydrogen atom or a halogen atom, preferably a chlorine atom and n is 1 or 2, with the proviso that two at least of the groups $R_5$, $R_6$ and $R_7$ represent a hydrogen atom and that, when n is 2, one at least of the groups $R_2$ and $R_3$ is not a hydrogen atom.

The pharmaceutically acceptable acid addition salts of the compounds of formula I such as, for example, the hydrochlorides, dihydrochlorides and fumarates, are also included within the scope of the invention.

The compounds of formula I, wherein $R_1$ represents a methyl radical, are considered under their racemic or optically active form.

The invention is also concerned with a process for preparing the compounds of formula I.

The compounds of the invention may be prepared by reacting an appropriately substituted indole derivative, represented by the general formula:

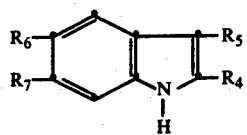

wherein $R_4$, $R_5$, $R_6$ and $R_7$ have the same meanings as in formula I, with sodium hydride and by reacting the derivative so obtained with a halogenated compound, represented by the general formula:

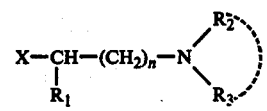

wherein X represents a halogen atom, preferably a chlorine or bromine atom and $R_1$, $R_2$, $R_3$ and n have the same meanings as in formula I.

The compounds of formula I, wherein n is 1, may alternatively be prepared by reacting an appropriately substituted derivative of formula II with sodium hydride and by reacting the compound so obtained with a halogenated derivative represented by the general formula:

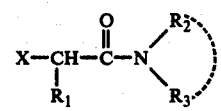

wherein X represents a halogen atom, preferably a chlorine or bromine atom, and $R_1$, $R_2$ and $R_3$ have the same meanings as in formula I, to give a compound represented by the general formula:

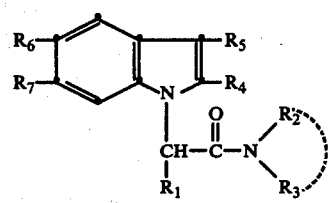

which is reduced by Li Al H$_4$, optionally in the presence of aluminium chloride.

The halogenated compounds of formulae III and IV are condensed on the sodium derivative of indole in various organic solvents such as, for example, benzene, toluene, 1,2-dimethoxy-ethane, bis (2-methoxy-ethyl) ether and particularly in N,N-dimethylformamide.

The compounds of formula I, wherein $R_1$ represents a hydrogen atom may alternatively be prepared by reacting an acid derivative represented by the general formula:

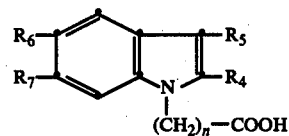

wherein $R_4$, $R_5$, $R_6$, $R_7$ and n have the same meanings as in formula I, with an amine of the general formula:

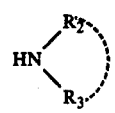

wherein $R_2$ and $R_3$ have the same meanings as in formula I, in the presence of triethylamine and ethyl chloroformiate, to give an amide of the general formula:

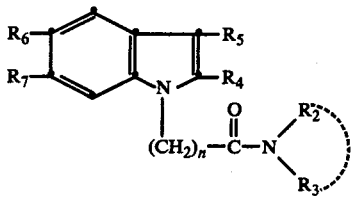

VIII wherein $R_2$, $R_3$, $R_4$, $R_5$, $R_6$, $R_7$ and n have the same meanings as in formula I, which is reduced by Li Al H$_4$, in the presence of aluminium chloride, to give the required compound of formula I.

Furthermore, 1-(3'-dimethylamino-propyl)-2-phenyl-5-hydroxy-indole may also be prepared by reacting 1-(3'-dimethylamino-propyl)-2-phenyl-5-methoxy-indole, this latter compound having been prepared by the general method, with hydrobromic or hydriodic acid.

1-(3'-dimethylamino-propyl)-2-phenyl-5-carboxy-indole may be prepared by acid hydrolysis of 1-(3'-dimethylamino-propyl)-2-phenyl-5-cyano-indole, prepared by the general method from 2-phenyl-5-cyano-indole, itself prepared by reacting potassium cyanide with the derivative of formula II in which $R_4$ represents a phenyl group and $R_6$ a bromine atom.

1-(3'-dimethylamino-propyl)-2-phenyl-5-amino-indole may be obtained by catalytic hydrogenation of 1-(3'-dimethylamino-propyl)-2-phenyl-5-nitro-indole, this latter compound having been prepared by the general method.

1-(3'-dimethylamino-propyl)-2-phenyl-5-methylamino-indole may be prepared by reacting 1-(3'-dimethylamino-propyl)-2-phenyl-5-amino indole, prepared as hereabove, with ethyl chloroformiate and by reducing the compound so obtained with Li Al H$_4$.

By the method hereabove described, but starting from 1-(3'-dimethylamino-propyl)-2-phenyl-5-methylamino-indole, 1-(3'-dimethylamino-propyl)-2-phenyl-5-dimethylamino-indole may also be prepared.

The compounds of formula VI, wherein n is 1, may be prepared by reacting an appropriately substituted derivative of formula II with ethyl chloroacetate and saponifying the ester obtained to form the required compound of formula VI.

The compounds of formula VI, wherein n is 2, may be prepared by reacting an appropriately substituted derivative of formula II with acrylonitrile, in the presence of N-benzyl-trimethylammonium hydroxide in dioxane, to obtain a compound represented by the general formula:

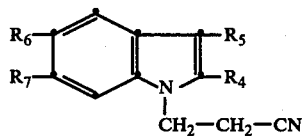

IX which is hydrolysed in an acid medium to form the required compound of formula VI.

The compounds of formula II, wherein $R_5$ represents a hydrogen atom or an alkyl radical, may be prepared by the FISCHER Indole Synthesis, which is described, for instance, in French Pat. No. 2,273,841 or, when $R_5$ represents a hydrogen atom, by the BISCHLER Indole Synthesis which is also described in the above-mentioned French Patent.

The indole derivatives of formula II, wherein $R_5$ represents an acyl radical, may be prepared by the VILSMEIER method, starting from an appropriately substituted indole derivative. This method is described by RAISON in J. Chem. Soc. 3319 (1949).

The compounds of formula II, wherein $R_5$ represents a methylthio or ethylthio radical, may be prepared by reacting an appropriately substituted indole derivative with thiourea, in the presence of ethanol and water, and then with dimethylsulphate or diethylsulphate.

The compounds of formula II, wherein $R_4$ represents a phenyl group and $R_6$ a nitro group, may alternatively be prepared by nitrating 2-phenylindole with nitric acid, in the presence of concentrated sulphuric acid.

The halogenated compounds of formula III may be prepared by reacting an appropriately substituted compound of the formula:

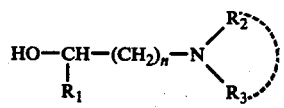

X wherein $R_1$, $R_2$, $R_3$ and n have the same meanings as in formula I, with thionyl chloride, in the presence of heptane and N,N-dimethylformamide.

The compounds of formula X are either known compounds, having been described in Berichte, by LADENBURG: 14, 1878 (1881) et 14, 2408 (1881), BEREND: 17, 512 (1884), GABRIEL and COLMAN: 40, 425 (1907), BRAUN: 49, 969 (1916) and BRAUN, BRAUNSDORF and RATH: 55, 1666 (1922) or may be prepared by the methods described in these publications.

The halogenated compounds of formula IV are either known compounds or may be prepared by well-known methods.

The compounds of formula I have been found to possess valuable pharmacological properties which are likely to render them useful in human and veterinary therapy.

In particular, they have been found to present psychotropic properties producing marked thymoanaleptic effects on the central nervous system.

Another object of the invention is, therefore, the use of the compounds of formula I or of their pharmaceutically acceptable acid addition salts, in human therapy as antidepressive and antiaggressive agents and in veterinary therapy as antiaggressive agents.

Amongst the most widely used antidepressants at present, particular mention may be made of the tricyclic thymoanaleptics such as imipramine, or 5-(3-dimethylamino-propyl)-10,11-dihydro-5H-dibenz [b,f] azepine.

This latter compound, which has a marked stimulating effect on mood, unfortunately presents, when used at active doses, undesirable side-effects such as, for instance, profuse sweating with sudden flashes, difficulties in optical accommodation, dryness of the mouth and urinary retentions.

Another interesting tricyclic thymoanaleptic is iprindole or 5-(3-dimethylamino propyl)-6, 7, 8, 9, 10, 11-hexahydro-5H-cycloocta [b] indole, which possesses not only very marked antidepressive properties but also weaker anticholinergic properties than imipramine.

Unfortunately, iprindole produces very pronounced hepato-toxic effects which may cause serious cases of icterus.

The compounds of the invention possess antidepressive properties of the iprindole type, but do not present the major disadvantages of this molecule.

Iprindole, although a tricyclic compound, is very different from the imipramine-like derivatives while the compounds of the invention, which are bicyclic compounds, very surprisingly present the same beneficial properties as iprindole, without producing the same undesirable side-effects.

The pharmacological study of the antidepressive effect of a substance is very difficult because it is naturally impossible to find a depressed animal or to induce depression in an animal.

However, over the years, many experimental models of depression have been developed by pharmacologists.

The new substances to be tested are submitted to these models and their effects compared to the effects of a well-known antidepressive agent which has already proved to be active in human therapy.

The compounds of the invention have been compared to the most closely related, chemically speaking, antidepressant, namely iprindole.

For the sake of clarity, the compounds of the invention which have been tested are numbered as follows:

1-(3'-Dimethylamino-propyl)-2-phenyl-indole (1)
1-(3'-Piperidino-propyl)-2-phenyl-indole (2)
1-(2'-Dibenzylamino-ethyl)-2-phenyl-indole (3)
1-(3'-Dimethylamino-propyl)-2-phenyl-5-chloro-indole (4)
1-(3'-Dimethylamino-propyl)-2-phenyl-6-chloro-indole (5)
1-(3'-Dimethylamino-propyl)-2-phenyl-5-nitro-indole (6)
1-(3'-Dimethylamino-propyl)-2-phenyl-5-methoxy-indole (7)
1-(3'-Dimethylamino-propyl)-2-phenyl-5-bromo-indole (8)
1-(3'-Dimethylamino-propyl)-2-phenyl-5-methyl-indole (9)
1-(3'-Dimethylamino-propyl)-2-phenyl-3-acetyl-indole (10)
1-(3'-Piperidino-propyl)-2-phenyl-3-acetyl indole (11)
1-(3'-Dimethylamino-propyl)-2-phenyl-3-methylthio-indole (12)
1-(2'-Diethylamino-ethyl)-2-phenyl-3-acetyl-indole (13)
1-(2'-Diethylamino-ethyl)-2-phenyl-3-methylthio-indole (14)
1-(3'-Dimethylamino-propyl)-2-phenyl-3-pentanoyl-indole (15)
1-(3'-Dimethylamino-propyl)-2-phenyl-3-methyl-indole (16)
1-(3'-Dimethylamino-propyl)-2-phenyl-3-ethyl-indole (17)
1-(3'-Dimethylamino-propyl)-2-phenyl-3-isopropyl-indole (18)
1-(3'-Dimethylamino-propyl)-2-(2',4'-dimethyl-phenyl)-indole (19)
1-(3'-Dimethylamino-propyl)-2,3-diisopropyl-indole (20)
1-(3'-Dimethylamino-propyl)-2-cyclohexyl-indole (21)
1-(2'-Diethylamino-ethyl)-2-cyclohexyl-indole (22)
1-(3'-Piperidino-propyl)-2-cyclohexyl-indole (23)
1-(3'-Dimethylamino-propyl)-2-cyclopentyl-indole (24)
1-(3'-Piperidino-propyl)-2-cyclopentyl-indole (25)
1-(2'-Cyclohexyleneimino-ethyl)-2-cyclopentyl-indole (26)
1-(2'-Diethylamino-ethyl)-2-cyclopentyl-indole (27)
1-(3'-Piperidino-propyl)-2-cyclopropyl-indole (28)
1-(3'-Dimethylamino-propyl)-2-(1'-methyl-cyclopropyl)-indole (29)
1-(3'-Dimethylamino-propyl)-2-cyclopropyl-indole (30)
1-(3'-Dimethylamino-propyl)-2-phenyl-5-amino-indole (31)
1-(3'-Dimethylamino-propyl)-2-phenyl-5-hydroxy-indole (32)
1-(3'-Dimethylamino-propyl)-2-phenyl-5-methylamino-indole (33)
1-(3'-Dimethylamino-propyl)-2-phenyl-5-dimethylamino-indole (34)
1-(3'-Dimethylamino-propyl)-2-phenyl-5-carboxy-indole (35)
1-(2'-Morpholino-ethyl)-2-phenyl-indole (36)
1-(2'-N-methylpiperazinyl-ethyl)-2-phenyl-indole (37)
1-(2'-Amino-ethyl)-2-phenyl-indole (38)
1-(2'-N-methylamino-ethyl)-2-phenyl-indole (39)
1-(3'-N-methylamino-propyl)-2-phenyl-indole (40)
1-(2'-Diethylamino-1'-methyl-ethyl)-2-phenyl-indole (41)

Pharmacological trials have been undertaken with the compounds listed hereabove and the following results were obtained:

1. Toxicity

Batches of ten mice were given an oral dose of 500 mg/kg of the compound to be studied and the percentages of deaths occurring within 48 hours after administration were noted.

The following results were obtained:

TABLE I

| Compound | Death % | Compound | Death % | Compound | Death % |
|---|---|---|---|---|---|
| 1 | 20 | 15 | 40 | 29 | 20 |
| 2 | 0 | 16 | 20 | 30 | 0 |
| 3 | 0 | 17 | 60 | 31 | 100 |
| 4 | 0 | 18 | 100 | 32 | 40 |
| 5 | 20 | 19 | 0 | 33 | 20 |
| 6 | 20 | 20 | 0 | 34 | 20 |
| 7 | 20 | 21 | 0 | 35 | 40 |
| 8 | 20 | 22 | 0 | 36 | 20 |
| 9 | 40 | 23 | 0 | 37 | 0 |
| 10 | 0 | 24 | 0 | 38 | 60 |
| 11 | 20 | 25 | 0 | 39 | 0 |
| 12 | 0 | 26 | 0 | 40 | 0 |
| 13 | 20 | 27 | 40 | 41 | 20 |
| 14 | 0 | 28 | 40 | Iprindole | 20 |

2. Determination of thymoanaleptic properties

The antagonist action of the compounds of the invention on the effects of reserpine was determined.

It is well known that reserpine sometimes provokes true depressive states when used in human therapy (treatment of arterial hypertension) while, when administered to an animal, it provokes a spectacular syndrome, mainly hypothermia, ptosis and catatonia.

These differents effects of reserpine are antagonized by the known antidepressants and the antireserpinic action of the compounds of the invention have been compared to that of iprindole.

An aqueous solution or an oily suspension, containing 100 mg/kg of the compound to be tested, was administered by oral route to batches of 5 male rats of the OFA strain weighing from 150 to 200 g. Thirty minutes later, 5 mg/kg of reserpine was administered by intraperitoneal route to the animals.

The following observations were made:

a. Inhibition of ptosis

Ptosis was evaluated for each eye and the results noted as a percentage of inhibition in comparison with the reserpine-induced ptosis of the control animals (which had not received the compound to be tested).

The following scale was used and the results are listed in the Table given hereunder:

0 = 0 to 20% of inhibition
1 = 20 to 40% of inhibition
2 = 40 to 60% of inhibition
3 = 60 to 80% of inhibition
4 = 80 to 100% of inhibition

TABLE II

| Compound | Inhibition | Compound | Inhibition | Compound | Inhibition |
|---|---|---|---|---|---|
| 1 | 1 | 13 | 1 | 31 | 1 |
| 3 | 1 | 14 | 1 | 33 | 2 |
| 6 | 1 | 15 | 1 | 34 | 1 |
| 7 | 1 | 16 | 1 | 35 | 1 |
| 8* | 1 | 17 | 1 | 39 | 1 |
| 10 | 1 | 20 | 2 | Iprindole | 1 |
| 12 | 2 | 21 | 1 | | |

*a dose of 25 mg/kg by intraperitoneal route was used.

These figures shows that the activity of the compounds of the invention is at least equal to that of iprindole, while compounds 12, 20 and 33 are even superior.

b. Inhibition of catatonia

The stretched-wire test was used to evaluate reserpine-induced catatonia. The front paws of the rats were placed on a horizontally streched-wire, situated at 15 cm from the ground and the animals which maintained the position so given for at least 30 seconds were considered to be catatonic.

The same scale as hereabove was used to express the percentage of inhibition in comparison with the control animals.

The following results were obtained:

TABLE III

| Compound | Inhibition | Compound | Inhibition | Compound | Inhibition |
|---|---|---|---|---|---|
| 1 | 2 | 18 | 1 | 33 | 1 |
| 4 | 1 | 19 | 1 | 34 | 1 |
| 6 | 1 | 20 | 1 | 35 | 1 |
| 8* | 1 | 24 | 1 | 36 | 1 |
| 12 | 1 | 27 | 1 | 37 | 1 |
| 14 | 1 | 29 | 1 | 38 | 2 |
| 16 | 2 | 30 | 1 | 39 | 1 |
| 17 | 2 | 31 | 2 | 40 | 1 |

TABLE III-continued

| Compound | Inhibition | Compound | Inhibition | Compound | Inhibition |
|---|---|---|---|---|---|
| | | | | Iprindole | 1 |

*a dose of 25 mg/kg by intraperitoneal route was used.

In this test also, the compounds of the invention were found to be least as active as iprindole, compounds 1, 16, 17, 31 and 38 being superior.

c. Inhibition of hypothermia

Rectal temperature was measured means of a probe. Inhibition of hypothermia, inferior to 0.5° C. in comparison with the control animals was considered as nil.

With the exception of Compound 22, the compounds of the invention were found to have no effect on reserpine-induced hypothermia. Iprindole did not exert any effect either.

d. Conclusion

Taking into account the overall results, it may be concluded that Compounds 1, 12, 16, 17, 20, 31 and 33 present greater antireserpine properties than iprindole, while the other compounds may be considered as equivalent to iprindole.

3. Determination of anticholinergic properties a. Antagonist action with respect to tremorine

The anticholinergic effect of the compounds of the invention (or rather the absence of such an effect) was studed by evaluating their antagonist action with respect to tremorine.

This study was also carried out by comparing the compounds of the invention to iprindole which is an antidepressant considered as being clinically devoid of anticholinergic properties, said properties giving rise, as stated above, to undesirable side-effects.

Thirty minutes after the administration per os of the compound to be tested, a dose of 10 mg/kg of tremorine was administered by intraperitoneal route to batches of 10 male mice of the OF1 strain. The doses of compounds of the invention are indicated in Table IV hereunder.

The effects of the tremorine have been separated into central effects (trembling, akinesia) and peripheral effects (weeping, hypersalivation, sedation and diarrhoea).

The method of EVERETT, which is described in Nature, 177, 238 (1956), was used.

Results were noted 30 minutes after administration of the tremorine and expressed in percentage of inhibition in accordance with the above scale.

The following results were obtained:

TABLE IV

| Compound | Dose mg/kg | Central effects | Peripheral effects | Compound | Dose mg/kg | Central effects | Peripheral effects |
|---|---|---|---|---|---|---|---|
| 1 | 50 | 2 | 2 | 22 | 100 | 1 | 0 |
| 2 | 100 | 1 | 1 | 23 | 100 | 2 | 2 |
| 3 | 100 | 0 | 0 | 24 | 100 | 1 | 1 |
| 4 | 100 | 1 | 0 | 25 | 100 | 2 | 1 |
| 5 | 100 | 1 | 0 | 26 | 100 | 1 | 1 |
| 6 | 100 | 0 | 0 | 27 | 100 | 2 | 1 |
| 7 | 100 | 3 | 2 | 28 | 100 | 0 | 1 |
| 8 | 100 | 1 | 1 | 29 | 100 | 2 | 1 |
| 9 | 100 | 0 | 0 | 30 | 100 | 1 | 1 |
| 10 | 100 | 1 | 0 | 31 | 100 | 1 | 1 |
| 11 | 100 | 1 | 1 | 32 | 100 | 2 | 2 |
| 12 | 100 | 0 | 0 | 33 | 100 | 1 | 3 |
| 13 | 100 | 0 | 0 | 34 | 100 | 1 | 1 |
| 14 | 100 | 0 | 0 | 35 | 100 | 0 | 0 |

TABLE IV-continued

| Compound | Dose mg/kg | Central effects | Peripheral effects | Compound | Dose mg/kg | Central effects | Peripheral effects |
|---|---|---|---|---|---|---|---|
| 15 | 100 | 0 | 1 | 36 | 100 | 0 | 0 |
| 16 | 100 | 2 | 1 | 37 | 100 | 3 | 3 |
| 17 | 100 | 1 | 0 | 38 | 100 | 0 | 0 |
| 18 | 100 | 0 | 2 | 39 | 100 | 0 | 0 |
| 19 | 100 | 0 | 0 | 40 | 100 | 0 | 1 |
| 20 | 100 | 1 | 1 | 41 | 100 | 1 | 1 |
| 21 | 100 | 1 | 1 | Iprindole | 100 (oral route) | 3 | 3 |

These results show that the compounds of the invention are markedly less anticholinergic than iprindole whereas the latter is already considered as clinically devoid of such properties.

Only Compound 37 was found to be equivalent to iprindole.

b. Antagonist effect with respect to prochlorperazine

Tests were also performed with a view to determining the percentage of inhibition, by the compounds of the invention, of catatonia induced by a neuroleptic, namely prochlorperazine.

This test also reveals the presence (or the absence) of anticholinergic properties in an antidepressant.

The compound to be tested was administered by oral route to batches of 5 male rats of the OFA strain and, thirty minutes later, a dose of 12.5 mg/kg of prochlorperazine was administered by intraperitoneal route.

The intensity of catatonia was evaluated by the stretched-wire test and the results noted as a percentage of inhibition in accordance with the previously used scale.

These results are given hereunder:

TABLE V

| Compound | Dose mg/kg | Inhibition | Compound | Dose mg/kg | Inhibition |
|---|---|---|---|---|---|
| 1 | 50 | 2 | 22 | 75 | 1 |
| 2 | 75 | 1 | 23 | 100 | 0 |
| 3 | 75 | 0 | 24 | 75 | 1 |
| 4 | 75 | 2 | 25 | 100 | 2 |
| 5 | 75 | 1 | 26 | 100 | 1 |
| 6 | 75 | 0 | 27 | 75 | 2 |
| 7 | 75 | 0 | 28 | 100 | 0 |
| 8 | 75 | 1 | 29 | 75 | 2 |
| 9 | 100 | 0 | 30 | 75 | 2 |
| 10 | 75 | 0 | 31 | 100 | 1 |
| 11 | 75 | 1 | 32 | 75 | 0 |
| 12 | 75 | 1 | 33 | 100 | 2 |
| 13 | 75 | 1 | 34 | 50 | 1 |
| 14 | 75 | 1 | 35 | 50 | 0 |
| 15 | 100 | 0 | 36 | 75 | 1 |
| 16 | 100 | 1 | 37 | 75 | 2 |
| 17 | 100 | 1 | 38 | 100 | 1 |
| 18 | 100 | 2 | 39 | 100 | 1 |
| 19 | 100 | 1 | 40 | 100 | 2 |
| 20 | 100 | 2 | 41 | 75 | 2 |
| 21 | 75 | 1 | Iprindole | 75 | 2 |

As in the previous test, the compounds of the invention were found to be less anticholinergic than iprindole with the exception, however, of Compounds 4, 24, 27, 29, 30, 37 and 41 which were found to be equivalent to iprindole.

c. Conclusion

In these two tests, only Compound 37 proved to be equivalent to iprindole, all the other compounds being less anticholinergic than iprindole.

4. Potentiation of the stereotypies induced by amphetamine

It is known that amphetamine induces stereotypies in the rat and it is commonly admitted that this is due to stimulation of the dopaminergic receptors and inhibition of the re-uptake of dopamine in the neuron.

It is also known that the thymoanaleptics potentiate these stereotypies.

Once again, the compounds of the invention were compared to iprindole, a well-known thymoanaleptic.

Batches of 5 male rats of the OFA strain were given by oral route 50 mg/kg of the compound to be tested and, thirty minutes later, 10 mg/kg of amphetamine sulphate were administered by intraperitoneal route to the animals.

Note was taken of the intensity of the stereotypies 6 hours after administration of the amphetamine, in accordance with the HALLIWELL scale, described in Brit. J. Pharmacol. 23, 330 (1964).

The results are expressed in percentage of potentiation in comparison with the control anmials, in accordance with the following scale:
0 = from 0 to 20% of potentiation
1 = from 20 to 40% of potentiation
2 = from 40 to 60% of potentiation
3 = from 60 to 80% of potentiation The following results were obtained:

TABLE VI

| Compound | Potentiation | Compound | Potentiation |
|---|---|---|---|
| 1 | 3 | 22 | 3 |
| 2 | 3 | 24 | 3 |
| 5 | 3 | 25 | 3 |
| 7 | 3 | 27 | 3 |
| 10 | 3 | 29 | 3 |
| 11 | 3 | 31 | 3 |
| 13 | 3 | 33 | 3 |
| 14 | 3 | 34 | 3 |
| 15 | 3 | 37 | 3 |
| 21 | 3 | Iprindole | 3 |

It may be observed that the compounds of the invention as well as iprindole potentiate the effects of amphetamine to a very marked degree.

5. Potentiation of the toxicity of yohimbine

It is well known that most of the tricyclic antidepressants potentiate the toxicity of yohimbine.

The action of the compounds of the invention on the toxicity of yohimbine was therefore determined.

Batches of 10 to 20 male mice of the OF1 strain were given by oral or intraperitoneal route the compound to be tested and, thirty minutes later, a dose of 25 mg/kg of yohimbine was administered by sub-cutaneous route.

The results are expressed as a percentage of potentiation in comparison with the control animals, in accordance with the above scale:

TABLE VII

| Compound | Dose mg/kg | Potentiation |
|---|---|---|
| 15 | 125 | 1 |
| 17 | 125 | 1 |
| 19 | 125 | 2 |
| 25 | 125 | 2 |
| 26 | 125 | 1 |
| 31 | 125 | 2 |
| 33 | 100 | 2 |
| 34 | 100 | 1 |
| 38 | 125 | 3 |
| 40 | 100 | 1 |

These figures confirm that the compounds of the invention, like the known tricyclic antidepressants, potentiate the toxicity of yohimbine.

6. Determination of antiaggressive properties

The antiaggressive properties of the compounds of the invention were determined by means of the killer-rats test, in accordance with the method of KARLI, Behaviour, 10, 81 (1956).

Rats which immediately killed three mice introduced one after another into their cage were selected and batches of 6 animals were constituted.

The rats were given the compound to be tested by intraperitoneal route and one hour later three mice were successively introduced into the cage.

The results were noted as a percentage of inhibition in comparison with the control animals, in accordance with the scale which was used for the study of the antireserpine properties.

TABLE VIII

| Compound | Dose mg/kg | Inhibition |
|---|---|---|
| 1 | 20 | 2 |
| 6 | 40 | 1 |
| 7 | 60 | 2 |
| 10 | 20 | 1 |
| 11 | 20 | 1 |
| 31 | 60 | 3 |
| 31 | 40 | 2 |
| 33 | 40 | 3 |
| 34 | 40 | 3 |
| 40 | 40 | 1 |
| Iprindole | 40 | 1 |
| Iprindole | 60 | 2 |

These figures show that the compounds of the invention possess more powerful antiaggressive properties than iprindole, with the exception of Compounds 6 and 40 which may be considered as equivalent to iprindole.

7. Determination of analgesic properties

The analgesic action of the compounds of the invention was determined by means of the KOSTER test, Fed. Proc. 18, 412 (1959).

The compound to be tested was administered by oral route to batches of 12 female mice, weighing from 13 to 17 g, fasting from the day before administration.

Sixty minutes later, a 1%-solution of acetic acid (0.2 ml/20 g of weight) was injected by intraperitoneal route. The number of stretching movements was noted during the 20 minutes following the injection.

The results are expressed in percentage of inhibition in comparison with the control animals, in accordance with the above scale.

TABLE IX

| Compound | Dose mg/kg | Inhibition |
|---|---|---|
| 1 | 200 | 3 |
| 16 | 200 | 3 |
| 17 | 200 | 2 |
| 18 | 50 | 1 |
| 19 | 200 | 2 |
| 31 | 200 | 3 |
| 40 | 50 | 2 |
| Iprindole | 100 | 2 |

These results show that the compounds of the invention are at least equivalent to iprindole and, in several cases, are even superior.

8. Local anaesthetic action

Guinea pigs were given by sub-cutaneous route 0.2 ml of a physiologic solution containing 0.5% of the compound to be tested, the solution being injected into two sites marked on the backs of the animals.

Note was taken of the number of stimulations of the cornea which did not provoke any closing of the eyelids, at periods of 5, 10, 15, 20, 25 and 30 minutes after the injection.

Six stimulations were carried out for each period of time and the results were expressed in percentage of inhibition in comparison with the control animals, in accordance with the above scale:

TABLE X

| Compound | Inhibition | Compound | Inhibition |
|---|---|---|---|
| 1 | 3 | 23 | 3 |
| 6 | 3 | 25 | 3 |
| 7 | 3 | 27 | 2 |
| 9 | 3 | 28 | 2 |
| 12 | 3 | 29 | 2 |
| 14 | 3 | 30 | 3 |
| 16 | 3 | 31 | 3 |
| 17 | 3 | 37 | 3 |
| 19 | 3 | 38 | 3 |
| 21 | 3 | 39 | 3 |

These results show that the compounds of the invention have a very marked local anaesthetic action.

9. Determination of hepato-toxicity

A three-week sub-acute toxicity study was carried out on the rat with Compound 31 and iprindole, using a daily oral dose of 150 mg/kg.

The results of the analysis (Table XI) show that Compound 31 is much less aggressive with respect to the liver than iprindole.

| Batch | Urea g/l | Glucose g/l | Cholesterol g/l | Lipids g/l | Proteins g/l | SGOT [1] mIU | SGPT [2] mIU | Bilirubine mg/l | Histology |
|---|---|---|---|---|---|---|---|---|---|
| Control | 0.42 ± 0.05 | 1.22 ± 0.10 | 0.84 ± 0.14 | 4.0 ± 0.2 | 59.3 ± 1.2 | 50.0 ± 7.0 | 20.1 ± 3.0 | 3.5 ± 0.7 | Nothing to report |
| Iprindole | 0.66 ± 0.22 | 1.26 ± 0.12 | 1.08 ± 0.16 | 5.4 ± 0.9 | 67.0 ± 1.6 | 90.5 ± 59.5 | 44.6 ± 28.3 | 4.3 ± 1.0 | Foci of hepatic necrosis |
| Compound 31 | 0.53 ± 0.10 | 1.19 ± 0.13 | 0.81 ± 0.07 | 4.0 ± 0.3 | 62.8 ± 1.8 | 54.3 ± 8.7 | 28.0 ± 7.6 | 2.6 ± 0.7 | Microresicular centrolobular hepatic steatosis |

| Batch | Urea g/l | Glucose g/l | Cholesterol g/l | Lipids g/l | Proteins g/l | SGOT[1] mIU | SGPT[2] mIU | Bilirubine mg/l | Histology |
|---|---|---|---|---|---|---|---|---|---|
| | | | | | | | | | (50%) |

[1] Serum succinoglutarate oxalate transaminase
[2] Serum succinoglutarate pyruvate transaminase It will be appreciated that for therapeutic use the compounds of the invention will normally be administered in the form of a pharmaceutical or veterinary composition comprising as an essential active ingredient at least one compound of formula I or a pharmaceutically acceptable acid addition salt thereof, in association with a pharmaceutical carrier or excipient therefor.

The carrier may be, for example, one at least of the ingredients selected from the following: lactose, starches, talc, magnesium stearate, polyvinylpyrrolidone, alginic acid, colloidal silica and microcrystalline cellulose.

Advantageously for clinical use, the composition is made up in a dosage unit form adapted for the desired mode of administration. The dosage unit may be, for example, a coated- or uncoated-tablet, a hard- or soft-gelatin capsule, a suspension, a powder, or a syrup for oral administration, a suppository for rectal administration or a solution for parenteral administration.

The following Examples illustrate the preparation of the compounds of the invention:

EXAMPLE 1

1-(3'Dimethylamino-propyl)-2-phenyl-indole a. Preparation of 1-chloro-3-dimethylamino-propane hydrochloride

Under vigorous stirring and at a temperature of 0° C., 103 g (1 mol) of 3-dimethylamino-propanol, 750 ml of heptane and 6.5 ml of dimethylformamide were reacted with 87 ml (1.2 mol) of thionyl chloride to give a yellowish white precipitate which became oily.

The solvent was evaporated off, 150 ml of methanol were added and the reaction medium was evaporated to dryness to give 1-chloro-3-dimethylaminopropane hydrochloride which was stored under this form.

The base was then regenerated just before the operation of alkylation of 2-phenyl-indole. In this way, 1-chloro-3-dimethylamino-propane was obtained. Boiling point: 30°–31° C. (13 mm/Hg).

By following the same procedure but using the appropriate starting-products the compounds listed hereunder were prepared:

| Compound | Boiling point ° C |
|---|---|
| 1-chloro-3-diethylamino-propane | 45 (13 mm/Hg) |
| 1-chloro-3-piperidino-propane | 84–87 (13 mm/Hg) |
| 1-chloro-2-dimethylamino-ethane | (not analysed) |
| 1-chloro-2-hexamethyleneimino-ethane | (not analysed) |
| 1-chloro-2-pyrrolidino-ethane | (not analysed) |
| 1-chloro-2-dibenzylamino-ethane | (not analysed) | b. Preparation of 1-(3'-dimethylamino-propyl)-2-phenyl-indole

While stirring and under any nitrogen atmosphere, a solution of 25 ml of dry dimethylformamide containing 19.3 g (0.1 mol) of 2-phenyl-indole was mixed with a suspension of 2.9 g (0.12 mol) of sodium hydride in 50 ml of dry dimethylformamide, the temperature of the mixture being maintained between 10° and 15° C.

The duration of the operation of addition was determined by the intensity of the release of hydrogen and was about 15 minutes.

The mixture was allowed to rise to room temperature and 14 g (0.1 mol) of 1-chloro-3-dimethylamino-propane were added and allowed to react for 10 hours at room temperature, or for 4 hours at 50° C.

With a view to improving yield, the advancement of the reaction was controlled by thin-layer chromatography, with a mixture of hexane/ethyl acetate/methanol (70/28/2) as eluent, under an ammonia-saturated atmosphere and on a silica support.

If the reaction happened to be incomplete, a slight excess of 1-chloro-3-dimethylamino-propane was added while the reaction time was increased.

As soon as the reaction was complete, the medium was poured into an iced solution of hydrochloric acid and was washed with ether in order to eliminate the non-alkylated 2-phenyl-indole.

The base was regenerated from its hydrochloride by means of a 20%-solution of sodium hydroxide and was extracted with ether, washed with water and dried over magnesium sulphate and the solvent was evaporated off.

After recrystallization from a mixture of dimethyl-formamide and water, 1-(3'dimethylamino-propyl)-2-phenyl-indole was obtained.

Yield: 70%. Melting Point: 52° C.

The hydrochloride was obtained by treating an ethereal solution of the base with a gaseous stream of dry hydrochloric acid. The hydrochloride precipitated and was filtered and recrystallized from isopropanol to give 1-(3'-dimethylamino-propyl)-2-phenyl indole hydrochloride.

Yield: 95%. Melting point: 200° C.

By following the same procedure but using the appropriate starting-products, the compounds listed hereunder were prepared in the form of a base, a hydrochloride or a fumarate.

This latter salt was obtained by dissolving 0.02 mol of the base in 200 ml of pure methanol and by adding to the solution 2.32 g (0.02 mol) of fumaric acid. The fumarate precipitated almost immediately and the methanolic solution was boiled until dissolution of the precipitate.

If necessary, dissolution was completed by adding gradually dimethylformamide and the solution was finally treated with activated carbon, filtered and allowed to crystallize.

The following products were obtained:

| Compound | Melting Point ° C | Yield % |
|---|---|---|
| 1-(3'-piperidino-propyl)-2-phenyl- | 240 | 65 |

-continued

| Compound | Melting Point °C | Yield % |
|---|---|---|
| indole hydrochloride | (isopropanol) | |
| 1-(3'-dimethylamino-propyl)-2-(2',4'-dimethyl-phenyl)-indole acid fumarate | 90 (methanol) | 76 |
| 1-(3'-dimethylamino-propyl)-2-cyclopropyl-indole acid fumarate | 153 (methanol) | 66 |
| 1-(3'-piperidino-propyl)-2-cyclopropyl)-indole acid fumarate | 143 (methanol) | 78 |
| 1-(3'-dimethylamino-propyl)-2-(1'-methyl-cyclopropyl)-indole acid fumarate | 191 (methanol) | 72 |
| 1-(3'-dimethylamino-propyl)-2-cyclopentyl-indole acid fumarate | 148 (methanol) | 75 |
| 1-(3'-dimethylamino-propyl)-2-cyclohexyl-indole acid fumarate | 183 (methanol) | 72 |
| 1-(3'-piperidino-propyl)-2-cyclohexyl-indole | 67 (methanol) | 90 |
| 1-(3'-dimethylamino-propyl)-2-phenyl 5-chloro-indole | 90 (hexane) | 75 |
| 1-(3'-dimethylamino-propyl)-2-phenyl-6-chloro-indole hydrochloride | 220 (isopropanol) | 70 |
| 1-(3'-dimethylamino-propyl)-2-phenyl-5-bromo-indole hydrochloride | 200 (isopropanol) | 70 |
| 1-(3'-dimethylamino-propyl)-2-phenyl-5-methyl-indole | 80 (purification by conversion to hydrochloride) | 60 |
| 1-(3'-dimethylamino-propyl)-2-phenyl-5-methoxy-indole hydrochloride | 185 (isopropanol) | 75 |
| 1-(3'-dimethylamino-propyl)-2-phenyl-5-cyano-indole | not analysed | |
| 1-(3'-dimethylamino-propyl)-2-phenyl 5-nitro-indole | 90 (cyclohexane) | 83 |
| 1-(3'-dimethylamino-propyl)-2-phenyl-3-acetyl-indole | 109 (heptane) | 85 |
| 1-(3'-piperidino-propyl)-2-phenyl-3-acetyl-indole hydrochloride | 240 (isopropanol) | 90 |
| 1-(3'-piperidino-propyl)-2-cyclopentyl-indole acid fumarate | 151-157 (methanol) | 76 |
| 1-(3'-dimethylamino-propyl)-2-phenyl-3-pentanoyl-indole hydrochloride | 190 (isopropanol) | 70 |
| 1-(3'-dimethylamino-propyl)-2-phenyl-3-methyl-indole acid fumarate | 174 (methanol) | 68 |
| 1-(3'-dimethylamino-propyl)-2-phenyl-3-ethyl-indole | 69 (ethanol-water 60/40) | 90 |
| 1-(3'-dimethylamino-propyl)-2-phenyl-3-isopropyl-indole acid fumarate | 166 (methanol) | 72 |
| 1-(3'-dimethylamino-propyl)-2,3-diisopropyl-indole acid fumarate | 173-175 (methanol) | 64 |
| 1-(2'-dimethylamino-ethyl)-2-phenyl-3-acetyl-indole | 105 (water) | 62 |
| 1-(2'-cyclohexyleneimino-ethyl)-2-phenyl-indole acid fumarate | 212 (ethanol) | 75 |
| 1-(2'-dibenzylamino-ethyl)-2-phenyl-indole | 103 (hexane) | 90 |
| 1-(2'-pyrrolidino-ethyl)-2-phenyl-indole | 77 (hexane) | 70 |
| 1-(2'-diethylamino-ethyl)-2-cyclopentyl-indole acid fumarate | 171 (methanol) | 76 |
| 1-(2'-cyclohexyleneimino-ethyl)-2-cyclopentyl-indole acid fumarate | 195 (methanol) | 75 |
| 1-(2'-diethylamino-ethyl)-2-cyclohexyl-indole acid fumarate | 197 (methanol) | 72 |
| 1-(2'-cyclohexyleneimino-ethyl)-2-cyclohexyl-indole acid fumarate | 205-206 (methanol) | 68 |

EXAMPLE 2

1-(3'methylamino-propyl)-2-phenyl-indole hydrochloride a. Preparation of 1-(2'-cyano-ethyl)-2-phenyl-indole 6 ml of N-benzyl-trimethylammonium hydroxide and 26 ml of acrylonitrile were successively added to 72 g (0.37 mol) of 2-phenyl-indole in 200 ml of dioxane.

The mixture was allowed to stand for one night at 60° C. in a thermostated water-bath and the reaction medium was placed in a freezer until crystallization of the final product. After filtration and recrystallization three times from ethanol, 1-(2'-cyano-ethyl)-2-phenyl-indole was obtained.

Yield: 80%. Melting Point: 90° C.

b. Preparation of 3-(2'-phenyl-1'-indolyl)-propionic acid 1-(2'-cyano-ethyl)-2-phenyl-indole obtained hereabove was refluxed in 36%-hydrochloric acid and almost all the acid precipitated from the hot medium.

The acid was filtered out and purified by transformation into its sodium salt. After recrystallization from ethanol, 3-(2'-phenyl-1'-indolyl)-propionic acid was obtained.

Yield: 85%. Melting Point: 129° C.

c. Preparation of 3-(2'-phenyl-1'-indolyl)-N-methylproprionamide 26.5 g (0.1 mol) of 3-(2'phenyl-1'-indolyl)-propionic acid was stirred in 50 ml of anhydrous tetrahydrofuran and 14 ml of triethylamine were added. The temperature was maintained between −5° C. and −10° C. by means of a mixture of carbon-dioxide ice and acetone and 10 ml of ethylchloroformiate in a small quantity of tetrahydrofuran were poured into the solution, care being taken that the temperature did not exceed 0° C. The medium was allowed to stand for 30 minutes at −5° C. and methylamine, previously cooled to −10° C., was added.

Stirring was continued for some hours and, while stirring, 600 ml of a cold aqueous 5%-solution of sodium hydroxide was poured into the reaction medium. The oil which formed was extracted with ether and the solvent was finally evaporated off under reduced pressure.

The amide so obtained was recrystallized from isopropanol to give 3-(2'-phenyl-1'-indolyl)-N-methylpropionamide.

Yield: 75%. Melting Point: 126° C.

d. Preparation of 1-(3'-N-methylamino-propyl)-2-phenol-indole

While stirring at room temperature, 5.56 g (0.02 mol) of 3-(2'-phenyl-1'-indolyl)-N-methylpropionamide, in solution in a minimum of tetrahydrofuran, were poured into a mixture containing 2.66 g (0.02 mol) of aluminium chloride, 3.05 g (0.08 mol) of Li Al H$_4$ and 100 ml of tetrahydrofuran.

At the end of the operation of addition, the mixture was refluxed for 5 hours, was allowed to cool and was slowly hydrolysed with small pieces of ice under nitrogen atmosphere. The gel which formed was vigorously stirred in the presence of ether, was filtered out and washed several times with ether.

The ethereal phases were collected and evaporated off, but not to dryness. The product was taken up in ether, washed with water and dried over magnesium sulphate.

1-(3'-methylamino-propyl)-2-phenyl-indole hydrochloride was obtained by treating the ethereal solution with a gaseous stream of dry hydrochloric acid and filtering out the precipitate which was finally recrystallized from isopropanol.

Yield: 72%. Melting Point: 187° C.

EXAMPLE 3

1-(3'-Dimethylamino-propyl)-2-phenyl-5-hydroxyindole 7 g (0.23 mol) of 1-(3'-dimethylamino-propyl)-2-phenyl-5-methoxyindole, prepared as in Example 1, were dissolved in 70 ml of 57%-hydriodic acid.

The temperature increased slightly corresponding to the formation of the amine hydriodide. The reaction medium was stirred for two hours on a boiling water-bath and the solution clarified progressively and was poured into water.

The solution was neutralized to pH7 with sodium hydroxide and was extracted with ether.

The ethereal solution was dried over magnesium sulphate and concentrated under reduced pressure.

The crude product was recrystallized from a mixture of cyclohexanebenzene (95/5) to give 1-(3'-dimethylamino-propyl)-2-phenyl-5-hydroxyindole.

Yield: 85%. Melting Point: 130° C.

EXAMPLE 4

1-(3'-dimethylamino-propyl)-2-phenyl-5-carboxyindole hydrochloride 1-(3'-dimethylamino-propyl)-2-phenyl-5-cyanoindole, prepared as in Example 1, was refluxed for 5 hours in hydrochloric acid and the aqueous solution was concentrated under reduced pressure.

1-(3'-dimethylamino-propyl)-2-phenyl-5-carboxyindole hydrochloride precipitated, was filtered out and recrystallized from a mixture of ethanol-heptane.

Yield: 72%. Melting Point: 205° C.

EXAMPLE 5

1-(3'-dimethylamino-propyl)-2-phenyl-5-amino-indole

While stirring, 32.3 g (0.1 mol) of 1-(3'-dimethylamino-propyl)-2-phenyl-5-nitro-indole, prepared as in Example 1, was mixed with 15 g (0.3 mol) of hydrazine hydrate, 300 ml of pure absolute ethanol and a small quantity of Raney Nickel.

The reaction was allowed to proceed slowly at 35° C. for one hour and its degree of advancement was controlled by thin-layer chromatography.

The solution was filtered and the ethanol was eliminated under reduced pressure. 1-(3'-dimethylamino-propyl)-2-phenyl-5-amino-indole precipitated and was collected with a yield of 92%.

This substance was purified either by obtaining the hydrochloride in an aqueous solution and washing the salt with ether and regenerating the base, or by recrystallization from a mixture of hexane-ethanol.

Melting Point: 126° C.

1-(3'-dimethylamino-propyl)-2-phenyl-5-amino-indole dihydrochloride was obtained by dissolving the pure base in a mixture of isopropanol-ether 50/50 and, while stirring with a magnetic stirrer, by allowing hydrochloric gas to bubble through the solution, which had first been slightly cooled. The precipitate which formed was filtered out, washed with isopropanol, then with heptane and finally was recrystallized from isopropanol.

Yield: 95%. Melting Point: decomposition at about 220° C.

EXAMPLE 6

1-(3'-dimethylamino-propyl)-2-phenyl-5-methylamino-indole hydrochloride a. Preparation of 1-(3'-dimethylamino-propyl)-2-phenyl-5-ethoxycarboxamidoindole 4.08 g (0.376 mol) of freshly distilled ethyl-chloroformiate was poured at room temperature and drop-by-drop into a solution of 11 g (0.367 mol) of 1-(3'-dimethylamino-propyl)-2-phenyl-5-amino-indole, prepared as in Example 5, in 150 ml of dry ether and stirring was maintained for 2 hours, still at room temperature.

The precipitate which formed was filtered out and washed several times with ether, it was then dissolved in 200 ml of water. The aqueous solution was then washed three times with ether and the base was obtained with a 10%-solution of sodium hydroxide.

The solution was extracted with ether and the organic phase was washed with water and dried over magnesium sulphate. The ether was evaporated off and the product which was obtained was recrystallized from cyclohexane containing a few drops of ethanol. 8.9 g of crude product were obtained and purified by chromatography on a basic alumina column, with ether as eluent, to give 8.6 g of 1-(3'-dimethylamino-propyl)-2-phenyl-5-ethoxycarboxamido-indole. Yield: 63%.

b. Preparation of 1-(3'-dimethylamino-propyl)-2-phenyl-5-methylamino-indole dihydrochloride A solution of 16.8 g (0.046 mol) of 1-(3'-dimethylamino-propyl)-2-phenyl-5-ethoxycarboxamido-indole in 100 ml of dry tetrahydrofuran was added, at room temperature, to a suspension of 6.1 g (0.16 mol) of Li Al H$_4$ in 150 ml of dry tetrahydrofuran. The mixture was allowed to stand for one hour at room temperature and was progressively heated until reflux of the tetrahydrofuran.

Reflux was maintained for 5 hours and the mixture was allowed to cool. The reaction medium was then hydrolysed by means of small pieces of ice, was stirred in the presence of 500 ml of ether and was filtered. The mineral residue was washed with ether and the ethereal fractions were collected and evaporated off.

The product obtained was purified by obtaining the hydrochloride and regenerating the base by means of a diluted solution of sodium hydroxide and extracting the base with ether. The ethereal solution was dried and the dihydrochloride was obtained directly by treating the solution with a gaseous stream of dry hydrochloric acid. The white precipitate was recrystallized from isopropanol to give 1-(3'-dimethylamino-propyl)-2-phenyl-5-methylamino-indole dihydrochloride.

Yield 80%. Melting Point: 210°-220° C.

By following the same procedure but starting from 1-(3'-dimethylamino-propyl)-2-phenyl-5-methylamino-indole, 1-(3'-dimethylamino-propyl)-2-phenyl-5-dimethylamino-indole dihydrochloride was prepared.

Yield: 85%. Melting Point: 200° C. (decomposition).

EXAMPLE 7

1-(1'-methyl-2'-diethylamino-ethyl)-2-phenyl-indole a. Preparation of N,N-diethyl-2-(phenyl-2'-1'-indolyl)-propionamide

While stirring and under a nitrogen atmosphere, a solution of 19.3 g (0.1 mol) of 2-phenyl-indole in 25 ml of dimethylformamide was added to a suspension of 2.4 g (0.1 mol) of NaH in 50 ml of dimethylformamide. When all the hydrogen had been given off, 19.7 g (0.12 mol) of 2-chloro-N,N-diethylpropionamide were introduced at room temperature, the latter having been prepared by reacting, at 0° C. in ether, pure diethylamine with 2-chloro-propionic acid chloride and distilling the solution at 80°-82° C. under a pressure of 1 mm/Hg.

The reaction medium was heated to 60° C. and this temperature was maintained for 4 hours.

The solution was poured into a mixture of ice and water and was extracted with ether to give N,N-diethyl-2-(2'-phenyl-1'-indolyl)-propionamide.

Yield: 60%

This product was directly engaged in the following step and was not analysed.

b. Preparation of 1-(1'-methyl-2'-diethylamino-ethyl)-2-phenyl-indole

At room temperature and under nitrogen atmosphere, a solution of 27.7 g (0.09 mol) of N,N-diethyl-2-(2'-phenyl-1'-indolyl)-propionamide in 100 ml of dry ether was added to a suspension of 6.85 g (0.18 mol) of Li Al H$_4$ in 50 ml of dry ether.

The mixture was maintained for 1 hour at 20°-25° C. and was refluxed for 3 hours. The mixture was cooled in an ice-bath and was slowly hydrolysed by adding small pieces of ice. While vigorously stirring, 150 ml of ether were added and the solution was filtered. The ethereal phase was washed with water and then with hydrochloric acid.

The aqueous solution of the hydrochloride was washed with ether. The base was formed by adding a solution of sodium hydroxide, was extracted with ether and dried over magnesium sulphate.

The substance which was obtained gave two products when submitted to thin-layer chromatography.

These two products were separated by chromatography on a neutral alumina column, with petroleum ether/benzene as eluent.

1-(1'-methyl-2'-diethylamino-ethyl)-2-phenyl-indole was obtained with a yield of 67%. Melting Point: 190° C.

EXAMPLE 8

1-(2'-amino-ethyl)-2-phenyl-indole a. Preparation of (2-phenyl-1-indolyl)-acetic acid

While stirring and under nitrogen atmosphere, a solution of 20 g (0.105 mol) of 2-phenyl-indole in 50 ml of dimethylformamide was added to a suspension of 5.5 g (0.115 mol) of NaH in 100 ml of dimethylformamide, the release of hydrogen being controlled 16 g (0.13 mol) of ethyl-chloro-acetate were added and the reaction medium was heated to 70° C. for 3 hours with a waterbath. The mixture was then poured into water containing a small quantity of acetic acid and the solution was extracted with ether. The ethereal phase was washed several times with water and dried over magnesium sulphate.

The (2-phenyl-1-indolyl)-ethyl acetate which was obtained was saponified with a 20%-alcoholic solution of potassium hydroxide and the solvent was evaporated off.

The residue was dissolved in water and the 2-phenyl-indole which did not react was extracted with ether.

The aqueous phase was purified by boiling in the presence of activated carbon and acidified with hydrochloric acid to give a white precipitate which was recrystallized from ethanol.

b. Preparation of (2'-phenyl-indolyl-acetamide)

The same procedure as in Example 2c was used, but starting from (2-phenyl-1-indolyl)-acetic acid and adding liquid ammonia instead of methylamine, the reaction medium being first cooled to −20° C.

By following the same method but using the appropriate starting-products, the compounds listed hereunder were prepared:

| Compound | Melting Point | Yield % |
|---|---|---|
| N-methyl-(2-phenyl-1-indolyl)-acetamide | 190 (isopropanol) | 35 |
| N-[(2-phenyl-1-indolyl)-acetyl]-morpholine | 235 (toluene) | 60 |
| N-[(2-phenyl-1-indolyl)-acetyl]-N- | 175 | 45 |

| Compound | Melting Point | Yield % |
|---|---|---|
| methyl-piperazine | (cyclohexane + ethanol) | |
| N,N-dimethyl-(2-phenyl-1-indolyl)-acetamide | 161 (cyclohexane) | 70 |
| N,N-diethyl-(2-phenyl-1-indolyl)-acetamide | 128 (cyclohexane) | 72 | c. Preparation of 1-(2'-amino-ethyl)-2-phenyl-indole hydrochloride

The same procedure as in Example 2d was used but starting from the compounds prepared hereabove.

However, the product which was obtained was purified by obtaining the hydrochloride and regenerating the base which was dried and recrystallized.

Finally, 1-(2'-amino-ethyl)-2-phenyl-indole hydrochloride was obtained by allowing dry hydrochloric gas to bubble through an ethereal solution of the base and was recrystallized from isopropanol.

Yield: 75%. Melting Point: 222° C.

By following the same procedure but using the appropriate starting-products, the compounds listed hereunder were prepared:

| Compound | Melting Point °C | Yield |
|---|---|---|
| 1-(2'-methylamino-ethyl)-2-phenyl-indole hydrochloride | 197 (isopropanol) | 70 |
| 1-(2'-morpholino-ethyl)-2-phenyl-indole | 80 (hexane) | 65 |
| 1-(2'-N-methylpiperazinyl-ethyl)-2-phenyl-indole dihydrochloride | 180 (isopropanol) | 60 (last step) |
| 1-(2'-diethylamino-ethyl)-2-phenyl-indole acid oxalate | 180 (ethanol) | 72 |

EXAMPLE 10

1-(2'-Dimethylamino-ethyl)-2-phenyl-3-methylthio-indole a. Preparation of 2-phenyl-3-methylthio-indole A mixture containing 1000 ml of pure ethanol, 200 ml of water, 95 g (1.25 mol) of thiourea and 120.5 g (0.62 mol) of 2-phenyl-indole was heated to 50°-60° C. and 157.7 g (0.62 mol) of iodine were slowly added. The reaction medium was then allowed to cool to room temperature and 100 g of sodium hydroxide were added, care being taken that the temperature did not go beyond 30° C., by means of a bath of water and ice.

Thirty minutes later, a further 50 g of sodium hydroxide were added. 80 g of dimethyl sulphate were poured into the reaction medium which was refluxed for 30 minutes.

After cooling, the product was precipitated by adding cold water. The precipitate was filtered out abundantly washed with water, dried and recrystallized from a mixture of hexane/benzene to give 2-phenyl-3-methylthio-indole.

Yield: 87%. Melting Point: 103° C.

b. Preparation of 3-(2'-phenyl-3'-methylthio-1'-indolyl)-propionic acid

A solution of 24 g (0.1 mol) of 2-phenyl-3-methylthio-indole in 50 ml of dimethylformamide was reacted for 30 minutes with 2.4 g (0.1 mol) of NaH and 18.1 g (0.1 mol) of 3-bromo-ethyl-propionate were added. The reaction medium was allowed to stand for 4 hours at 35°-40° C., was poured into water and was extracted with ether. The ethereal phase was washed with water and the crude product obtained was saponified by refluxing in the presence of a 10%-ethanolic solution of sodium hydroxide. The solvent was evaporated off and the aqueous solution of the sodium salt was washed with ether.

The aqueous solution was finally acidified by a solution of hydrochloric acid and 3-(2'-phenyl-3'-methylthio-1'-indolyl)-propionic acid precipitated and was recrystallized from ethyl acetate.

c. Preparation of 3-(2'-phenyl-3'-methylthio-1'-indolyl)-N,N-dimethyl-propionamide The same method as in Example 2c was used, except that the acid obtained hereabove was reacted with dimethylamine instead of methylamine.

d. Preparation of 1-(3'-dimethylamino-propyl)-2-phenyl-3-methylthio-indole

The same method as in Example 2d was used, but starting from the above amide, to give 1-(3'-dimethylamino-propyl)-2-phenyl-3-methylthio-indole, of which the hydrochloride melted at 90° C.

By the same procedure but using the appropriate starting-products, 1-(2'-diethylamino-ethyl)-2-phenyl-3-methylthio-indole was also prepared.

Melting point of the hydrochloride: 167° C.

EXAMPLE 11

Tablets containing the following ingredients were prepared in accordance with known pharmaceutical techniques:

| Ingredient | mg/tablet |
|---|---|
| 1-(3'-dimethylamino-propyl)-2-phenyl-5-amino-indole | 30 |
| Starch, talc, magnesium stearate | q.s. 100 mg |

We claim:

1. A compound of the formula:

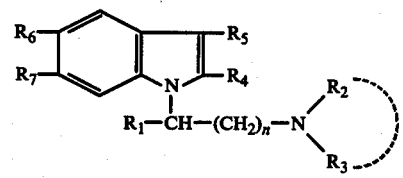

wherein $R_1$ represents a hydrogen atom, $R_2$ and $R_3$, which are the same or different, each represent a hydrogen atom, a methyl or ethyl radical, $R_4$ represents a phenyl radical, $R_5$ represents a hydrogen atom, $R_6$ represents an amino, methylamino or dimethylamino radical, $R_7$ represents a hydrogen atom, and n is 1 or 2 and its pharmaceutically acceptable acid addition salts.

2. 1-(3'-Dimethylamino-propyl)-2-phenyl-5-amino-indole and its pharmaceutically acceptable acid addition salts.

3. 1-(3'-Dimethylamino-propyl)-2-phenyl-5-methylamino-indole and its pharmaceutically acceptable acid addition salts.

4. 1-(3'-Dimethylamino-propyl)-2-phenyl-5-dimethylamino-indole and its pharmaceutically acceptable acid addition salts.

5. A pharmaceutical composition for treating pathological states of depression or aggressivity in a subject in need of such treatment, containing as essential active principle at least one compound of claim 1 or a pharmaceutically acceptable acid addition salt thereof in association with a pharmaceutical carrier or excipient therefor.

6. A pharmaceutical composition according to claim 5 containing as essential active principle 1-(3'-dimethylamino-propyl)-2-phenyl-5-amino-indole or a pharmaceutically acceptable acid addition salt thereof in association with a pharmaceutical carrier or excipient therefor.

7. A method of treating pathological states of depression or aggressivity in a subject in need of such treatment, said method consisting in administering to the said subject at least one compound of claim 1 or a pharmaceutically acceptable acid addition salt thereof.

8. A method of treating pathological states of depression or aggressivity in a subject in need of such treatment, said method consisting in administering to the said subject 1-(3'-dimethylamino-propyl)-2-phenyl-5-amino-indole or a pharmaceutically acceptable acid addition salt thereof.

* * * * *